(12) United States Patent
Kuroita et al.

(10) Patent No.: US 7,048,915 B2
(45) Date of Patent: May 23, 2006

(54) COMPOSITION FOR CELL-FREE PROTEIN SYNTHESIS

(75) Inventors: Toshihiro Kuroita, Tsuruga (JP);
Bunsei Kawakami, Tsuruga (JP);
Yoshihisa Kawamura, Tsuruga (JP);
Shigemichi Nishikawa, Kyoto (JP);
Yaeta Endo, Matsuyama (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 444 days.

(21) Appl. No.: 10/124,953

(22) Filed: Apr. 18, 2002

(65) Prior Publication Data

US 2003/0199076 A1    Oct. 23, 2003

(51) Int. Cl.
*A61K 33/00*    (2006.01)
*A61K 35/78*    (2006.01)
*C12P 21/06*    (2006.01)
*A01N 65/00*    (2006.01)

(52) U.S. Cl. .................... 424/68.1; 435/69.1; 435/183; 435/252.8; 435/325; 424/184.1; 424/600; 424/725

(58) Field of Classification Search ............... 435/68.1, 435/252.8, 183, 325, 69.1; 424/600, 184.1, 424/725
See application file for complete search history.

(56) References Cited

U.S. PATENT DOCUMENTS 6,653,463 B1 *   11/2003   Chen et al. ................ 536/23.6
2003/0162246 A1 *   8/2003   Endo et al. ................ 435/68.1

FOREIGN PATENT DOCUMENTS

WO    WO 98/02532    1/1998

OTHER PUBLICATIONS

Endo et al., "Production of an Enzymatic Active Protein Using a Continuous Flow Cell-Free Translation System," *Journal of Biotechnology*, 25, 221-230 (1992).
Erickson et al., "Cell-Free Translation of Messenger RNA in a Wheat Germ System," *Methods in Enzymology*, 96, 38-50 (1996).
Madin et al., "A Highly Efficient and Robust Cell-Free Protein Synthesis System Prepared from Wheat Embryos: Plants Apparently Contain a Suicide System Directed at Ribosomes," *Proceedings of the National Academy of Sciences of the United States of America*, 97 (2), 559-564 (Jan. 18, 2000).

* cited by examiner

*Primary Examiner*—Herbert J. Lilling
(74) *Attorney, Agent, or Firm*—Kilyk & Bowersox, P.L.L.C.

(57) ABSTRACT

The present invention provides a composition for cell-free protein synthesis, which is superior in storage stability in a freeze-dried state, more particularly a freeze-dryable or freeze-dried composition for cell-free protein synthesis, which contains a cell extract for cell-free protein synthesis and inositol, and a freeze-dryable or freeze-dried composition for cell-free protein synthesis containing a cell extract for cell-free protein synthesis, and a deliquescent material in a proportion of not more than 0.01 part by weight per part by weight of a protein in the composition; and a composition for cell-free protein synthesis superior in storage stability in a frozen state, more particularly a freezable or frozen composition for cell-free protein synthesis, containing a cell extract for cell-free protein synthesis and polyhydric alcohol.

10 Claims, 7 Drawing Sheets

COMPOSITION FOR CELL-FREE PROTEIN SYNTHESIS

TECHNICAL FIELD OF THE INVENTION

The present invention relates to a stabilized composition for cell-free protein synthesis. More particularly, the present invention relates to a freeze-dryable or freeze-dried composition for cell-free protein synthesis, which contains a cell extract for cell-free protein synthesis and inositol as a stabilizer, a freeze-dryable or freeze-dried composition for cell-free protein synthesis, which contains a cell extract for cell-free protein synthesis and a deliquescent material in a proportion of not more than 0.01 part by weight per part by weight of a protein in the composition, and to a freezable or frozen composition for cell-free protein synthesis, which contains a cell extract for cell-free protein synthesis and a polyhydric alcohol as a stabilizer.

BACKGROUND OF THE INVENTION

A method of cell-free protein synthesis includes taking components involved in biological protein synthesis out of the body and semi-artificially synthesizing a protein using a nucleic acid such as messenger RNA (mRNA) encoding the objective protein, energy sources such as ATP, GTP etc., and amino acid to be a starting material, but without using a cell. When compared to protein synthesis methods employed heretofore using recombinant microorganisms and cultured-cells, this method is advantageous in that (1) a protein that acts negatively on the body (except protein influential on the translation system) can be synthesized relatively easily, (2) the conditions can be determined easily (the use of microorganism etc. generally requires at least about one month for determination of the conditions), (3) unnatural amino acid can be used, and so on. In view of these advantages, it is expected that a method of cell-free protein synthesis will be widely used for various applications where many kinds of proteins need to be synthesized in a short time, production of a protein by a recombinant organism is difficult and so on.

The biomaterial to be used for a method of cell-free protein synthesis is frequently *Escherichia coli*, reticulocyte from mammal blood or wheat embryo. To date, various methods for preparing or utilizing cell extracts have been constructed. However, the protein synthesis activity of these cell extracts decreases when preserved at a temperature higher than −70° C. At present, therefore, the extract is typically frozen at −70° C. or below and preserved and transported at this temperature. In addition, protein synthesis requires various enzymes and factors of more than about 50 kinds including ribosome and the like, and stable supply of them requires a means to collectively stabilize a mixture of these components.

To meet the request, the technique for cold storage of cell extracts by freeze-drying has been developed in recent years. It is a general practice to use additives to facilitate stabilization by freeze-drying. As a result, trehalose has been reported to stabilize cell extracts during freeze-drying for cell-free protein synthesis (WO9802532). When additives are determined, stability during long-term storage is an important aspect. For confirmation of the stability during long-term storage, a storage stability test is generally done under harsh conditions (preservation at 25° C. or higher and the like), which is considered to well reflect the actual long-term storage stability. In the investigation by the present inventors, however, addition of trehalose failed to prevent degradation of the activity at 37° C., leaving uncertainty in a successful long-term preservation.

As a matter of fact, the storage stability of frozen cell extract for cell-free protein synthesis, particularly stabilization at around −30° C. to −15° C., which is a common preservation and transport temperature, has been scarcely studied heretofore. As the situation stands, there is a demand for additives more effective on the storage stability of cell extract for cell-free protein synthesis.

It is therefore an object of the present invention to provide a composition for cell-free protein synthesis, which is superior in storage stability in a freeze-dry state, and a composition for cell-free protein synthesis, which is superior in storage stability in a frozen state.

SUMMARY OF THE INVENTION

After screening various additives, the present inventors have found that inositol improves the storage stability of freeze-dried cell extracts for cell-free protein synthesis, and polyhydric alcohol improves the storage stability of frozen cell extracts for cell-free protein synthesis, and further that the amount of a deliquescent material below a certain level improves the storage stability of freeze-dried cell extracts for cell-free protein synthesis.

Accordingly, the present invention relates to a freeze-dryable or freeze-dried composition for cell-free protein synthesis, which comprises inositol and a cell extract for cell-free protein synthesis.

Preferably, the content of inositol in the above-mentioned composition is 0.3–3 parts by weight per part by weight of a protein in the composition.

Preferably, the above-mentioned composition further contains at least one kind of component selected from the group consisting of trehalose, mannitol and sucrose-epichlorohydrin copolymer.

Preferably, the content of a deliquescent material in the above-mentioned composition is not more than 0.01 part by weight per part by weight of the protein in the composition.

Preferably, the deliquescent material in the above-mentioned composition is potassium acetate and/or magnesium acetate.

Preferably, the cell extract for cell-free protein synthesis in the above-mentioned composition is derived from plant seed, *Escherichia coli* or reticulocyte from mammal blood.

Preferably, the cell extract for cell-free protein synthesis in the above-mentioned composition is derived from a plant seed selected from the group consisting of wheat, barley, rice, corn and spinach.

Preferably, the above-mentioned composition further contains a bioactive protein relating to the cell-free protein synthesis.

Preferably, the bioactive protein in the above-mentioned composition is at least one kind selected from the group consisting of creatine (phospho)kinase, pyruvate kinase, RNA polymerase and chaperone protein.

The present invention also relates to a freezable or frozen composition for cell-free protein synthesis, which contains a cell extract for cell-free protein synthesis and polyhydric alcohol.

Preferably, the content of polyhydric alcohol in the above-mentioned composition is 0.1–10 parts by weight per part by weight of protein in the composition.

Preferably, the polyhydric alcohol in the above-mentioned composition is at least one kind selected from the group consisting of inositol, glucitol, mannitol, xylitol, sucrose-epichlorohydrin copolymer, trehalose and sucrose.

Preferably, the cell extract for cell-free protein synthesis in the above-mentioned composition is derived from plant seed, *Escherichia coli* or reticulocyte from mammal blood.

Preferably, the cell extract for cell-free protein synthesis in the above-mentioned composition is derived from a plant seed selected from the group consisting of wheat, barley, rice, corn and spinach.

Preferably, the above-mentioned composition further contains a bioactive protein relating to a cell-free protein synthesis.

Preferably, the bioactive protein in the above-mentioned composition is at least one kind selected from the group consisting of creatine (phospho)kinase, pyruvate kinase, RNA polymerase and chaperone protein.

The present invention relates to a freeze-dryable or freeze-dried composition for cell-free protein synthesis, which contains a cell extract for cell-free protein synthesis and a deliquescent material in a proportion of not more than 0.01 part by weight per part by weight of a protein in the composition.

Preferably, the deliquescent material in the above-mentioned composition is potassium acetate and/or magnesium acetate.

Moreover, the present invention relates to a kit for cell-free protein synthesis, which contains any of the above-mentioned compositions and a material relating to the cell-free protein synthesis.

The present invention also relates to a method of cell-free protein synthesis, which comprises use of any of the above-mentioned compositions or kit.

Preferably, the above-mentioned method of cell-free protein synthesis is characterized by the use of a continuous supply system of amino acids and energy sources.

Preferably, the above-mentioned method of cell-free protein synthesis is characterized by the use of a dialysis method.

The present invention relates to a method for stabilizing a cell extract for cell-free protein synthesis, which comprises adding inositol to the cell extract for cell-free protein synthesis.

Preferably, in the above-mentioned stabilization method, the content of inositol is 0.3–3 parts by weight per part by weight of the protein in the cell extract.

The present invention moreover relates to a method for stabilizing a cell extract for cell-free protein synthesis, which comprises adding polyhydric alcohol to the cell extract for cell-free protein synthesis.

In the above-mentioned stabilization method, the content of the polyhydric alcohol is preferably 0.1–3 parts by weight per part by weight of the protein in the cell extract.

The present invention also relates to a method for stabilizing a cell extract for cell-free protein synthesis, which comprises setting a content of the deliquescent material in the cell extract for cell-free protein synthesis to not more than 0.01 part by weight per part by weight of a protein in the cell extract.

DETAILED DESCRIPTION OF THE INVENTION

Figure 1:
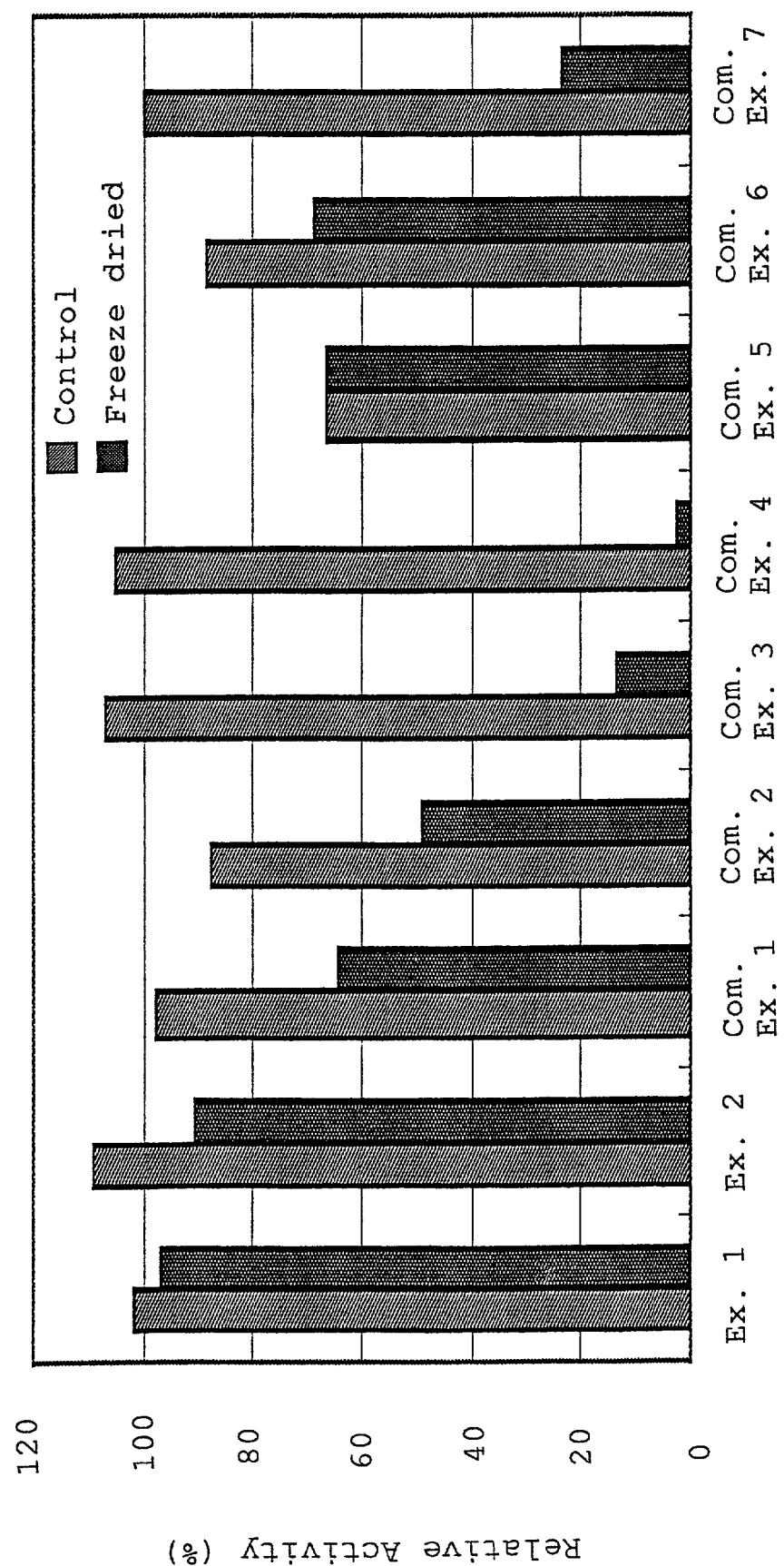
FIG. 1 shows the effect of each additive on the storage stability of a freeze-dried cell extract (wheat embryo extract), wherein Control shows a cell extract preserved for the same period of time as the sample in liquid nitrogen without freeze-drying, and Freeze-dried shows a cell extract preserved at 37° C. for 24 h after freeze-drying.

[Freeze-Dryable or Freeze-Dried Composition for Synthesis of Cell-Free Protein]

The freeze-dryable or freeze-dried composition for cell-free protein synthesis of the present invention is either a freeze-dryable (capable of being freeze-dried) composition or a composition in a freeze-dried state.

[1] Inositol-Containing Composition

This composition contains a cell extract for cell-free protein synthesis and inositol, and shows superior storage stability in a freeze-dry state by the action of the inositol.

The "cell extract for cell-free protein synthesis" in the above-mentioned composition is a solution containing a component (cell extract material) relating to the protein synthesis in the body, which is extracted from various cells, such as plant cell, animal cell, fungous cell, bacterial cell and the like, or tissues and the like, and which is applicable to cell-free protein synthesis (i.e., presence of a protein synthesis capability under cell-free conditions). This cell extract can be generally obtained by rupturing the above-mentioned cells, homogenizing the crushed cells in a buffer containing several kinds of salts for solubilizing a protein component and ribosome, centrifuging the homogenate to allow precipitation of the insoluble component, and removing a low molecular component derived from the cells by gel filtration and the like. While the constitution thereof varies depending on the biomaterial, preparation method and the like, in the case of wheat embryo cell extract to be mentioned below, for example, it generally contains a protein (20–60 mg/ml), transfer RNA (tRNA) (0.1–0.5 mg/ml) and ribosome as main components.

While the derivation of the above-mentioned cell extract for cell-free protein synthesis is not particularly limited, it is preferably a plant seed, *Escherichia coli* or reticulocyte from mammal blood, because of easy availability, available convenient preparation method, high protein synthesis capability and the like. For example, the plant of the "plant seed" is preferably wheat, barley, rice, corn or spinach, particularly preferably wheat. *Escherichia coli* preferably does not contain a plasmid, and K-1 strain-derived *Escherichia coli* is often used. For example, the mammal of the "reticulocyte from mammal blood" is preferably rabbit, mouse, rat or guinea pig. Of these, a cell extract derived from plant seed, preferably a seed of wheat, barley, rice, corn or spinach, particularly preferably wheat seed, is mentioned. A cell extract derived from an embryo without endosperm, particularly one derived from wheat embryo is preferable.

A cell extract derived from the embryo without endosperm (embryo extract), particularly wheat embryo extract, is almost free of inhibitors for protein synthesis localized in endosperm, such as ribosome specific glycosidase (tritin) and the like. When this extract is used for cell-free protein synthesis, a protein can be synthesized efficiently. This embryo extract can be obtained by purifying the embryo by ultrasonic cleaning of the embryo in an aqueous solution preferably according to the method of K. Madin et al. Proc. Natl. Acad. Sci. USA, 97(2), 559–564 (2000)) to wash the endosperm component, and treating the purified embryo according to a conventional method (e.g., A. H. Erickson et al. Meth. in Enzymol., 96, 38–50 (1996)).

The above-mentioned composition contains a protein derived from a cell extract (or added separately where necessary). The content thereof is free of any particularly limitation, but it is preferably 1–10 wt %, more preferably 2.5–5 wt %, of the whole composition before freeze-drying, and preferably 10–90 wt %, more preferably 25–70 wt %, of the whole composition after freeze-drying, in view of the storage stability in a freeze-dry state and easy handling. Where necessary, the protein content of the composition before freeze-drying may be made to fall within the above-mentioned range by a conventional method, such as gel filtration, dialysis and the like.

The protein content here is calculated by measuring the absorbance (260, 280, 320 nm) (see Examples below; the following protein content is measured by the same method).

The inositol in the above-mentioned composition acts as a stabilizer for the components contained in a cell extract in a freeze-dry state. The inositol is a general name of cyclohexanehexahydric alcohols having a molecular weight of 180.16, which are referred to as inosit, hexahydroxycyclohexane, cyclohexanehexol, cyclohexitol, meat sugar and the like, and 9 kinds of stereoisomers (myo-inositol, D(+)-inositol, L-(−)inositol, muco-inositol, scyll-inositol, cis-inositol, epi-inositol, allo-inositol and neo-inositol) are present. Myo-inositol, D(+)-inositol, L-(−)inositol, muco-inositol and scyll-inositol have been confirmed to be present in natural substances. Any stereoisomer can be used in the present invention, but in view of easy availability, myo-inositol is preferably used. The inositol permits concurrent use of two or more kinds of stereoisomers.

The content of inositol in the above-mentioned composition is preferably 0.3–3 parts by weight, more preferably 0.5–2 parts by weight, per part by weight of a protein contained in the composition. When it is less than 0.3 part by weight, sufficient storage stability may not be achieved in a freeze-dry state and the activity may be degraded due to moisture absorption, whereas when it exceeds 3 parts by weight, the protein synthesis reaction may be inhibited. The inositol can be preferably contained in the composition by adding an inositol solution (or powder) to the cell extract to make its content suitable or by substitution with a solution containing inositol by gel filtration, dialysis and the like.

The above-mentioned composition preferably contains, together with inositol, at least one kind of component selected from the group consisting of trehalose, mannitol and sucrose-epichlorohydrin copolymer (e.g., Ficoll (trademark); Amersham Biosciences Corp.). By the concurrent use thereof with inositol, the storage stability in a freeze-dry state can be improved without lowering the cell-free protein synthesis activity. The content thereof in this composition is preferably 0.1–3 parts by weight, more preferably 0.5–2 parts by weight, per part by weight of a protein contained in the composition, for the same reason as in the case of inositol.

The substance that shows deliquescence (deliquescent material) in the above-mentioned composition degrades the storage stability in a freeze-dry state. Therefore, its content is preferably not more than 0.01 part by weight, particularly not more than 0.005 part by weight, per part by weight of a protein contained in the composition. Examples of the deliquescent material include potassium acetate and magnesium acetate. The cell extract is generally prepared from cells using a solution (buffer) containing potassium acetate and/or magnesium acetate. Therefore, it contains potassium acetate at a level of about 100 mM and magnesium acetate at a level of about 5 mM. Thus, a cell extract is preferably subjected to gel filtration, dialysis and the like before freeze-drying, so that the freeze-dried composition will have a deliquescent material content within the above-mentioned range.

The above-mentioned composition preferably contains a bioactive protein relating to the cell-free protein synthesis. By the bioactive protein relating to the cell-free protein synthesis is meant an enzyme involved in regeneration of a substrate (particularly ATP), an enzyme involved in synthesis of RNA from template DNA, to be the template for protein synthesis, and chaperone proteins that form a three-dimensional structure of a protein. The enzyme involved in regeneration of a substrate (particularly ATP) is exemplified by creatine (phospho)kinase, pyruvate kinase and the like. The enzyme involved in the synthesis of RNA is exemplified by various RNA polymerases (T7, T3, SP6 RNA polymerase etc.). The chaperone proteins are exemplified by various chaperone proteins (DnaJ, DnaK, GroE, GroEL, GroES, HSP70 and the like). The bioactive proteins may be used in a combination of two or more kinds thereof.

The content of the above-mentioned bioactive protein in the above-mentioned composition is not particularly limited, but in view of the storage stability in a freeze-dry state and functionality, it is preferably 1–10 wt %, more preferably 2–5 wt %, of the whole content of the protein in the composition. The bioactive protein may be contained in the cell extract, but generally the amount thereof is not sufficient to allow full progress of the above-mentioned cell-free protein synthesis. Generally, therefore, it needs to be added during the cell-free protein synthesis. In the present invention, inositol, that acts as a stabilizer, can also stabilize the additionally provided bioactive protein in a freeze-dry state. Therefore, the bioactive protein can be added in advance to the composition. As a result, the step of addition of the bioactive protein can be omitted from the cell-free protein synthesis and the cost necessary for the production of a reagent can be preferably reduced.

It is possible to reinforce, where necessary, the non-protein component involved in the cell-free protein synthesis, which is contained in the above-mentioned composition. The non-protein component is a component originally contained in the cell extract for cell-free protein synthesis, which improves the protein synthesis performance when added. As this component, tRNA can be mentioned. The amount of this component to be used can be adequately determined depending on presumed conditions of cell-free protein synthesis, protein synthesis activity of the cell extract for cell-free protein synthesis, the kind of the synthesize protein and the like. In the case of tRNA, for example, it is generally 0.01–0.05 part by weight, preferably 0.02–0.04 part by weight, per part by weight of the protein in the composition.

The freeze-dry method and equipment to be used for freeze-drying of the above-mentioned composition are not particularly limited, but the container is preferably placed close to a container having good thermal conductivity, such as metal tray and the like, during freeze-drying. Particularly, when conducted in a microtube, the use of an aluminum block and the like formed into the shape of a microtube is preferable. During actual freeze-drying, a sample is preferably frozen at a temperature of not higher than −30° C. for 30 min or longer, depressurized with a vacuum pump, and the temperature of the metal plate (tray) is gradually increased. A heater may be used as necessary. The completion of the freeze-drying can be confirmed by the same temperature of the metal plate and the freeze-dried product. Nitrogen substitution as the last step is preferable.

The loss of each component due to freeze-drying is generally extremely small and of an ignorable level. Therefore, the weight ratio (concentration ratio) of each component before freeze-drying is generally the same as the weight ratio of the freeze-dried composition.

The above-mentioned composition is superior in storage stability in a freeze-dry state as compared to a conventional freeze-dried composition used for cell-free protein synthesis. For example, when the above-mentioned composition is freeze-dried and preserved at 2–10° C., the composition is generally stable for about 10–20 days, and when preserved at −35° C. to −15° C., generally stable for about 120–180 days. This means that under such preservation conditions, the cell-free protein synthesis activity is maintained by at least 80%.

[2] Composition Containing a Deliquescent Material Below Certain Level

This composition contains a cell extract for cell-free protein synthesis and a deliquescent material in a proportion of not more than 0.01 part by weight, preferably not more than 0.005 part by weight, per part by weight of the protein contained in the composition. The deliquescent material is exemplified by potassium acetate and magnesium acetate.

The "cell extract for cell-free protein synthesis" in the above-mentioned composition is exemplified by the above-mentioned inositol-containing composition.

The cell extract is generally prepared from cells using a solution (buffer) containing potassium acetate and/or magnesium acetate. Therefore, it contains potassium acetate at a level of about 100 mM and magnesium acetate at a level of about 5 mM. Thus, a cell extract is preferably subjected to gel filtration, dialysis and the like, so that the composition will have a deliquescent material content within the above-mentioned range. Alternatively, a cell extract is prepared from cells using a solution (buffer) without potassium acetate and/or magnesium acetate or a solution containing only a scarce amount thereof, so that the composition has a deliquescent material content within the above-mentioned range.

The above-mentioned composition preferably contains inositol. Examples of the inositol include those mentioned with regard to the above-mentioned inositol-containing composition, wherein its content is preferably 0.3–3 parts by weight, more preferably 0.5–2 parts by weight, per part by weight of a protein contained in the composition, for the same reason as in the case of the above-mentioned inositol-containing composition.

Like the above-mentioned inositol-containing composition, this composition preferably contains at least one kind of component selected from the group consisting of trehalose, mannitol and sucrose-epichlorohydrin copolymer (e.g., Ficoll (trademark); Amersham Biosciences Corp.). The content thereof in this composition is preferably 0.1–3 parts by weight, more preferably 0.5–2 parts by weight, per part by weight of a protein contained in the composition, for the same reason as for the above-mentioned inositol-containing composition.

The above-mentioned composition preferably contains a bioactive protein involved in cell-free protein synthesis. Examples of the bioactive protein include those mentioned with regard to the above-mentioned inositol-containing composition, which may be used in combination of two or more kinds thereof. The content of the above-mentioned bioactive protein is, as in the above-mentioned inositol-containing composition, preferably 1–10 wt %, more preferably 2–5 wt %, of the whole content of the protein in the composition.

It is possible to reinforce, where necessary, the non-protein component involved in the cell-free protein synthesis, which is contained in the above-mentioned composition. The non-protein component is exemplified by those mentioned with regard to the above-mentioned inositol-containing composition. The amount of this component to be used is, as in the above-mentioned inositol-containing composition, in the case of tRNA, for example, generally 0.01–0.05 part by weight, preferably 0.02–0.04 part by weight, per part by weight protein in the composition.

The freeze-dry method and equipment to be used for freeze-drying of the above-mentioned composition are those mentioned with regard to the above-mentioned inositol-containing composition.

Generally, the loss of each component due to freeze-drying is generally extremely small and of an ignorable level. Therefore, the weight ratio (concentration ratio) of each component before freeze-drying is generally the same as the weight ratio of the freeze-dried composition.

The above-mentioned composition is superior in storage stability in a freeze-dry state as compared to a conventional freeze-dried composition used for cell-free protein synthesis. For example, when the above-mentioned composition is freeze-dried and preserved at 2–10° C., the composition is generally stable for about 10–20 days, and when preserved at −35° C.–−15° C., generally stable for about 120–180 days. This means that under such preservation conditions, the cell-free protein synthesis activity is maintained in at least 80%.

[Freezable or Frozen Composition for Cell-Free Protein Synthesis]

The freezable or frozen composition for cell-free protein synthesis of the present invention is a freezable (or capable of being frozen) composition, or a composition in a frozen state. This composition is characterized in that it contains a cell extract for cell-free protein synthesis and polyhydric alcohol, and shows superior storage stability in a frozen state by the action of polyhydric alcohol.

The "cell extract for cell-free protein synthesis" in the above-mentioned composition is exemplified by those mentioned with regard to the above-mentioned freeze-dryable or freeze-dried composition for cell-free protein synthesis.

The protein content of the above-mentioned composition is preferably 1–10 wt %, more preferably 2.5–5 wt %, of the whole composition for storage stability in a frozen state, easy handling and the like.

The polyhydric alcohol in the above-mentioned composition is not particularly limited as long as plural hydrogens of hydrocarbon are substituted by hydroxyl group and exemplified by various natural or artificially synthesized sugars, sugar alcohol, polyethylene glycols, glycerol and the like. In view of storage stability and functionality, pentose, hexose and derivatives thereof (polymer and the like) are preferable. Of these, inositol, glucitol, mannitol, xylitol, sucrose-epichlorohydrin copolymer (e.g., Ficoll (trademark); Amersham Biosciences Corp.), trehalose and sucrose are preferable because they afford a composition superior in storage stabilization in a frozen state. More preferably, inositol, glucitol, xylitol and sucrose-epichlorohydrin copolymer are preferable because they not only afford a composition superior in storage stabilization in a frozen state, but exerts no adverse influence on cell-free protein synthesis activity. The polyhydric alcohol may be used in combination of two or more kinds thereof.

The polyhydric alcohol content of the above-mentioned composition is not particularly limited. In view of the storage stability in a frozen state, influence on cell-free protein synthesis reaction system, handling property and the like, it is preferably 0.1–10 parts by weight, more preferably 0.1–3 parts by weight, particularly preferably 0.5–2 parts by weight, per part by weight of a protein contained in the composition.

The above-mentioned composition preferably contains, like the above-mentioned freeze-dryable or freeze-dried composition, a bioactive protein involved in the cell-free protein synthesis. Examples of the bioactive protein include those mentioned above with regard to the freeze-dryable or freeze-dried composition. In view of the storage stability and functionality in a frozen state, the bioactive protein content is preferably 1–10 wt %, more preferably 2–5 wt %, of the whole protein contained in the composition.

Like the above-mentioned freeze-dryable or freeze-dried composition, it is possible to reinforce, where necessary, the non-protein component involved in the cell-free protein synthesis. The non-protein component includes those mentioned above with regard to the above-mentioned freeze-dryable or freeze-dried composition. The content of this component in the above-mentioned composition can be adequately determined depending on presumed conditions of cell-free protein synthesis, the kind of the synthesize protein and the like. It is generally 0.01–0.05 part by weight, preferably 0.02–0.04 part by weight, per part by weight protein in the composition.

The method for freezing the above-mentioned composition is not particularly limited and may follow a conventional method. It is preferable that the temperature reach the objective level as soon as possible.

The above-mentioned composition is superior in storage stability in a frozen state as compared to a conventional frozen composition used for cell-free protein synthesis. For example, when the above-mentioned composition is frozen and preserved at −35° C. to −15° C., the composition is generally stable for about 4–100 days, and when preserved at −70° C. to −35° C., generally stable for about 100–300 days. This means that under such preservation conditions, the cell-free protein synthesis activity is maintained by at least 80%.

[Kit for Cell-Free Protein Synthesis]

The composition of the present invention can constitute a kit for cell-free protein synthesis together with a material involved in the cell-free protein synthesis. The material involved in the cell-free protein synthesis includes a material that maintains protein synthesis stable and a material responsible for stabilization or improvement of the function of a synthesized protein. Examples thereof include bioactive protein involved in cell-free protein synthesis [enzyme involved in ATP regeneration (e.g., creatine (phospho)kinase, pyruvate kinase and the like), various RNA polymerases (e.g., T7, T3, and SP6 RNA polymerases and the like), chaperone protein (e.g., DnaJ, DnaK, GroE, GroEL, GroES and HSP70 and the like)], amino acid, energy source (ATP, GTP, creatine phosphate and the like), RNA (mRNA, tRNA and the like), protease inhibitor, (ribo)nuclease inhibitor and the like. This material may be used in combination of two or more kinds thereof.

The above-mentioned kit for cell-free protein synthesis can constitute a kit for ribosome display, together with reverse transcriptase, heat resistance DNA polymerase, primers, various deoxyribonucleoside triphosphates (dNTPs), various buffers (or polymerase chain reaction (PCR) reagent containing these). The kit for ribosome display refers to a method to utilize interaction, such as protein—protein interaction to separate the ternary complex, consisting of a target protein, a ribosome and an encoding mRNA, reverse-transcribe the mRNA thereof and amplify by PCR method, whereby the gene of a protein that interacts with the substance is isolated.

[Method of Cell-Free Protein Synthesis]

Using the composition of the present invention (inclusive of a kit for cell-free protein synthesis containing the composition), cell-free protein synthesis can be conducted. For example, the composition is added to a reaction system containing mRNA encoding the objective protein, amino acids that constitute the objective protein and energy source (ATP, GTP and the like), and the reaction mixture is heated to generally 20–40° C., preferably 23–30° C. to synthesize the objective protein.

When a continuous supply system of amino acids and energy sources is applied to the above-mentioned reaction system, a protein can be continuously synthesized. This continuous method of cell-free protein synthesis includes, for example, a method utilizing dialysis as a continuous supply system of amino acids and energy sources, that is, a method for dialyzing the above-mentioned reaction system against an external solution containing amino acids and energy sources (ATP, GTP and the like) (dialysis method). This dialysis method is preferably exemplified by the method described in Y. Endo et al., J. Biotech., 25, 221–230 (1992) and K. Madin et al. Proc. Natl. Acad. Sci. USA, 97(2), 559–564 (2000)). For example, the above-mentioned reaction system is placed in a dialysis apparatus having a dialysis membrane having a fractional molecular weight of 3,500–100,000, preferably 10,000–50,000, and dialyzed against a dialysis external solution (containing amino acids, energy sources (ATP, GTP and the like)) in a volume of 5 to 10-fold the volume of the reaction solution. The dialysis is conducted while stirring at generally 20–40° C., preferably 23–30° C., on periodic (generally every 24 h) exchange with new external solution. In addition, fresh mRNA of the objective protein may be periodically (generally every 24 h) supplied to the reaction solution.

[A Method for Stabilizing the Cell Extract for Cell-Free Protein Synthesis]

[1] Method Characteristically Containing Inositol

This method for stabilizing the cell extract for cell-free protein synthesis is characterized in that the cell extract contains inositol. This is a method for stabilizing the cell extract for cell-free protein synthesis in a freeze-dry state by the action of inositol. The inositol and cell extract for cell-free protein synthesis in this method are those mentioned above with regard to the freeze-dryable or freeze-dried composition. Similarly, the amount of inositol to be used is preferably 0.3–3 parts by weight, more preferably 0.5–2 parts by weight, per part by weight of a protein in the cell extract. Similarly, inositol can be contained in a cell extract for cell-free protein synthesis, as in the above-mentioned composition.

This method may contain, in addition to inositol, at least one kind of component selected from the group consisting of trehalose, mannitol and sucrose-epichlorohydrin copolymer, as in the above-mentioned freeze-dryable or freeze-dried composition, to improve storage stability in a freeze-dry state. According to this method, the content of the above-mentioned deliquescent material may be made to fall within the above-mentioned range, as in the case of the above-mentioned freeze-dryable or freeze-dried composition. Moreover, a bioactive protein associated with the above-mentioned cell-free protein synthesis and a non-protein component associated with the above-mentioned cell-free protein synthesis can be added. The amounts of these components are the same as those mentioned above with regard to the freeze-dryable or freeze-dried composition.

[2] Method Characteristically Containing Polyhydric Alcohol

This method for stabilizing the cell extract for cell-free protein synthesis is characterized in that the cell extract contains polyhydric alcohol. This is a method for stabilizing the cell extract for cell-free protein synthesis in a frozen state by the action of polyhydric alcohol. The polyhydric alcohol and cell extract for cell-free protein synthesis for this method are exemplified by those mentioned with regard to the above-mentioned freezable or frozen composition and, likewise, the amount of polyhydric alcohol to be used is preferably 0.1–10 parts by weight, more preferably 0.1–3 parts by weight, particularly preferably 0.5–2 part by weight, per part by weight of a protein in the cell extract. The polyhydric alcohol may be used in combination of two or more kinds thereof. According to this method, the above-mentioned bioactive protein associated with cell-free protein synthesis and the above-mentioned non-protein component associated with cell-free protein synthesis may be contained as in the above-mentioned freezable or frozen composition. The amounts thereof to be added are the same as in the above-mentioned freezable or frozen composition.

[3] Method Characteristically Containing Deliquescent Material in an Amount Below Given Level This method for stabilizing the cell extract for cell-free protein synthesis is a method for stabilizing the cell extract for cell-free protein synthesis in a freeze-dry state by controlling the amount of a deliquescent material in a cell extract for cell-free protein synthesis in a proportion of not more than 0.01 part by weight, preferably not more than 0.005 part by weight, per part by weight of the protein contained in the cell extract. The deliquescent material and cell extract for cell-free protein synthesis in this method are exemplified by those mentioned above with regard to the freeze-dryable or freeze-dried composition. The cell extract in this method may contain the above-mentioned bioactive protein associated with cell-free protein synthesis or the above-mentioned non-protein component associated with cell-free protein synthesis.

According to the above-mentioned method, inositol and at least one kind of component selected from the group consisting of trehalose, mannitol and sucrose-epichlorohydrin copolymer are preferably contained as in the above-mentioned freeze-dryable or freeze-dried composition, with the aim of improving the storage stability in a freeze-dry state. According to this method, moreover, the above-mentioned bioactive protein associated with cell-free protein synthesis and the above-mentioned non-protein component associated with cell-free protein synthesis may be added. The amounts of these to be added are the same as in the case of the above-mentioned freeze-dryable or freeze-dried composition.

The present invention is explained in detail in the following by referring to Examples, which are not to be construed as limitative.

The myo-inositol, trehalose, mannitol, glucitol, xylitol and sucrose used in Examples were purchased from Nacalai Tesque, Inc. and Ficoll 400 (trademark) was purchased from Amersham Biosciences Corp. In Examples, the following measurement methods were used.

[1] Batch Assay of Cell-Free Protein Synthesis Activity

An assay of protein synthesis activity by the batch method involved reaction under the following reaction conditions. First, sterile distilled water was added to a freeze-dried composition (sample) to be mentioned below to make the total amount 25 µl, whereby a test solution was prepared. As regards the frozen composition to be mentioned below, a solution after thawing was used as a test solution. Then, a solution containing a test solution, adjusted to be 25% (v/v) of the total volume, was prepared, which further contained 1000 units/ml ribonuclease inhibitor (RNasin; Toyo Boseki Kabushiki Kaisha), 30 mM HEPES-KOH (pH 7.6), 95 mM potassium acetate, 2.65 mM magnesium acetate, 2.85 mM dithiothreitol, 0.5 mg/ml creatine (phospho)kinase (Roche), 1.2 mM ATP, 0.25 mM GTP, 16 mM creatine phosphate, 0.38 mM spermidine, 20 kinds of L-amino acids (each 0.3 mM), 80 µg/ml Green fluorescent protein (GFP) mRNA with CAP (prepared according to the method of Y. Endo et al. (1992) J. Biotech., 25, 221–230), 50 mCi [U-$^{14}$C] leucine (166 mCi/mmol: Amersham Biosciences Corp.) (hereinafter to be referred to as reaction solution A). The reaction was carried out at 26° C. and, after a certain time, 5 µl therefrom was spotted on a 1 cm×0.5 cm square filter paper. The measurement of [U-$^{14}$C] leucine intake was performed by the method of Y. Endo et al. (J. Biotech., 25, 221–230 (1992)). To be specific, the filter was treated in cold 10% (w/v) trichloroacetic acid solution for 30 min to immobilize the protein, boiled in 5% (w/v) trichloroacetic acid for 10 min, and rinsed twice with this acid. The filter was treated with diethyl ether/ethanol (1:1) and diethyl ether for 5 min each. Clearsol I (3 ml, trademark; Nacalai Tesque, Inc.) was added and radioactivity was measured by a liquid scintillation counter (Packard). The activity was measured using a wheat embryo extract in the same lot, which had been preserved in liquid nitrogen for the same time as the sample, as a control and expressed in relative activity to the activity thereof as 100. As a control of each additive, each additive was added to the same concentration and preserved in liquid nitrogen for the same time as the sample without freeze-drying or freezing and used.

[2] Measurement of Protein Content in Cell Extract and Each Composition

The protein content in a cell extract and each composition (composition before freeze-drying (freezing) and composition after freeze-drying (freezing)) was calculated by measuring the absorbance (260, 280, 320 nm) of the protein solution. To be specific, a protein solution prepared by dissolving in sterile distilled water or diluting with sterile distilled water (e.g., cell extract is diluted 400-fold) as necessary was applied to measurement using photometer DU640 (nucleic acid measurement application, BECKMAN), with sterile distilled water as a blank. The calculation of the measured values of this apparatus is based on the Warburg-Christian method.

PRODUCTION EXAMPLE 1

Preparation of Wheat Embryo Extract (1) Isolation of Wheat Embryo

For an intact (having germinability) isolation method from a seed using a mill, floatation and a sieve, the method of Johnston et al. (F. B. Johnston et al. Nature, 179, 160–161 (1957)) was improved. Wheat seed (unsterilized) was cast in a mill (Rotor Speed Mill pulverisette 14, manufactured by Fritsh) at a rate of 100 g per min and the seed was softly crushed at 8000 r.p.m. This was again crushed at 6000 r.p.m. and passed through a sieve (mesh size 0.71 mm–1.00 mm) to give crude embryo fraction. The embryo having germinability was recovered from floating fraction by floatation using a mixture of carbon tetrachloride and cyclohexane (carbon tetrachloride:cyclohexane=2.5:1) and dried at room temperature to remove organic solvent. The impurities such as seed skin and the like contained in this embryo fraction were removed by adsorption to a member charged with static electricity, such as polyethylene plate and the like, and the 0.71 mm–0.85 mm fraction was separated using a sieve. To remove an endosperm component, the fraction was suspended in a 0.5% (w/v) solution of NP40 (Nonidet P40), which was a nonionic surfactant, according to the method of K. Madin et al. (K. Madin et al. Proc. Natl. Acad. Sci. USA, 97, 559–564 (2000)), and repeatedly washed with an ultrasonic cleaning machine until the washing solution did not become clouded. Lastly, this was subjected to ultrasonic cleaning with distilled water to purify the wheat embryo.

(2) Preparation of Wheat Embryo Extract

The wheat embryo extract and solution for protein synthesis were prepared according to a conventional method (A. H. Erickson et al., Meth. in Enzymol., 96, 38–50 (1996)). The following operation was conducted at 4° C. First, the washed wheat embryo was frozen by adding liquid nitrogen and completely pulverized with a pestle. An extract (80 mM HEPES-KOH (pH 7.8), 200 mM potassium acetate, 2 mM magnesium acetate, 4 mM calcium chloride, 8 mM dithiothreitol) obtained according to a partially-modified method of Patterson et al. was added at a rate of 1 ml per 1 g and stirred carefully to avoid foaming. The mixture was centrifuged at 30 k×g for 15 min, and subjected to buffer exchange by gel filtration using Sephadex G-25 column (Coarse) equilibrated with a solution (40 mM HEPES-KOH (pH 7.8), 0.6 mM L type amino acid (20 kinds), 100 mM potassium acetate, 5 mM magnesium acetate, 4 mM dithiothreitol). Lastly, a sample concentration was adjusted to 200 (A 260 nm)(Warburg-Christian method: 5.00 wt %), dispensed and freeze-preserved in liquid nitrogen.

[Effect of Each Additive on Storage Stability of Freeze-Dried Cell Extract (Wheat Embryo Extract)]

EXAMPLE 1

An aqueous solution (80 µl) of myo-inositol dissolved and adjusted to a concentration of 12.50 wt % in sterile distilled water was added to the wheat embryo extract (protein concentration 5.00 wt %, 100 µl) prepared in Production Example 1, in a 1.5 ml screw cap type microtube, and a mixture having a myo-inositol concentration of 5.50 wt % and a protein concentration of 2.75 wt % was prepared. The mixture was frozen in a freeze-dry machine (apparatus DF-03H; ULVAC, Inc.) at −35° C. for 1 h and depressurized to not more than 1 Torr using a vacuum pump. At this time, the microtube was fixed to an aluminum block cut off into a tube shape and the cap was loosened. The temperature was raised gradually overnight and, after confirmation of the same sample temperature and the temperature in the machine, the vacuum pump was turned off. The machine was filled with a nitrogen gas, allowed to reach the atmospheric pressure, and sealed in a nitrogen gas-filled state by tightly closing the cap of the microtube. In this way, a composition of a freeze-dried wheat embryo extract (hereinafter to be referred to as a freeze-dried composition) was prepared.

EXAMPLE 2 AND COMPARATIVE EXAMPLES 1–7

In the same manner as in Example 1, respective freeze-dried compositions shown in Table 1 were prepared (sterile distilled water was used instead of the aqueous solution containing additives in Comparative Example 7).

TABLE 1

| | | mixture final concentration | | freeze-dried composition content | |
|---|---|---|---|---|---|
| | additive | additive wt % | protein wt % | additive wt % | protein wt % |
| Example 1 | myo-inositol | 5.50 | 2.75 | 64.8 | 32.4 |
| Example 2 | myo-inositol | 2.75 | 2.75 | 47.9 | 47.9 |
| Comp. Ex. 1 | trehalose | 2.75 | 2.75 | 47.9 | 47.9 |
| Comp. Ex. 2 | mannitol | 2.75 | 2.75 | 47.9 | 47.9 |
| Comp. Ex. 3 | glucitol | 2.75 | 2.75 | 47.9 | 47.9 |
| Comp. Ex. 4 | xylitol | 2.75 | 2.75 | 47.9 | 47.9 |
| Camp. Ex. 5 | sucrose | 2.75 | 2.75 | 47.9 | 47.9 |
| Comp. Ex. 6 | Ficoll 400 | 2.75 | 2.75 | 47.9 | 47.9 |
| Comp. Ex. 7 | Not added | — | 2.75 | — | 92.0 |

(Storage Stability Test)

The respective freeze-dried compositions shown in Table 1 were preserved at 37° C. for 24 h and, according to the above-mentioned batch activity-assay method, the cell-free protein synthesis activity of each freeze-dried composition was measured. The results are shown in FIG. 1.

As shown in FIG. 1, the preservation at 37° C. for 24 h resulted in a decrease in the protein synthesis activity to about 20% of the freeze-dried composition (Comparative Example 7) without additives. In contrast, the freeze-dried compositions (Examples 1 and 2) containing myo-inositol retained activity of 90% or above. The freeze-dried composition (Comparative Example 1) containing trehalose conventional considered to provide a high stabilizing effect showed an activity decrease to 65%, showing considerable loss of activity as compared to myo-inositol. The sugar alcohols generally used as a stabilizer showed a still lower activity, wherein the residual activity ratios were 55% for mannitol (Comparative Example 2), 10% for glucitol (Comparative Example 3) and 2.5% for xylitol (Comparative Example 4). The freeze-dried composition (Comparative Example 5) containing sucrose showed superior storage stability, but without freeze-drying, the protein synthesis activity was lower than others, suggesting inhibition of protein synthesis by sucrose.

[Comparison of Effects of Inositol and Trehalose on Storage Stability of Freeze-Dried Compositions]

EXAMPLE 3 AND 4 AND COMPARATIVE EXAMPLES 8–10

In the same manner as in Example 1, the respective freeze-dried compositions shown in Table 2 were prepared (sterile distilled water was used instead of the aqueous solution containing additives in Comparative Example 8). The trehalose concentrations (10.00 wt % in Comparative Example 9 and 5.00 wt % in Comparative Example 10) were confirmed to provide the highest storage stabilization effect in WO9802532.

TABLE 2

| | additive | mixture final concentration | | freeze-dried composition content | |
|---|---|---|---|---|---|
| | | additive wt % | protein wt % | additive wt % | protein wt % |
| Example 3 | myo-inositol | 5.50 | 2.75 | 64.8 | 32.4 |
| Example 4 | myo-inositol | 2.75 | 2.75 | 47.9 | 47.9 |
| Comp. Ex. 8 | not added | — | 2.75 | — | 92.0 |
| Comp. Ex. 9 | trehalose | 10.00 | 2.75 | 77.0 | 21.2 |
| Comp. Ex. 10 | trehalose | 5.00 | 2.75 | 62.6 | 34.4 |

(Storage Stability Test)

The respective freeze-dried compositions shown in Table 2 were preserved at 37° C. for 24 h and, according to the above-mentioned batch activity assay method, the cell-free protein synthesis activity of each freeze-dried composition was measured. The results are shown in FIG. 2.

Figure 2:
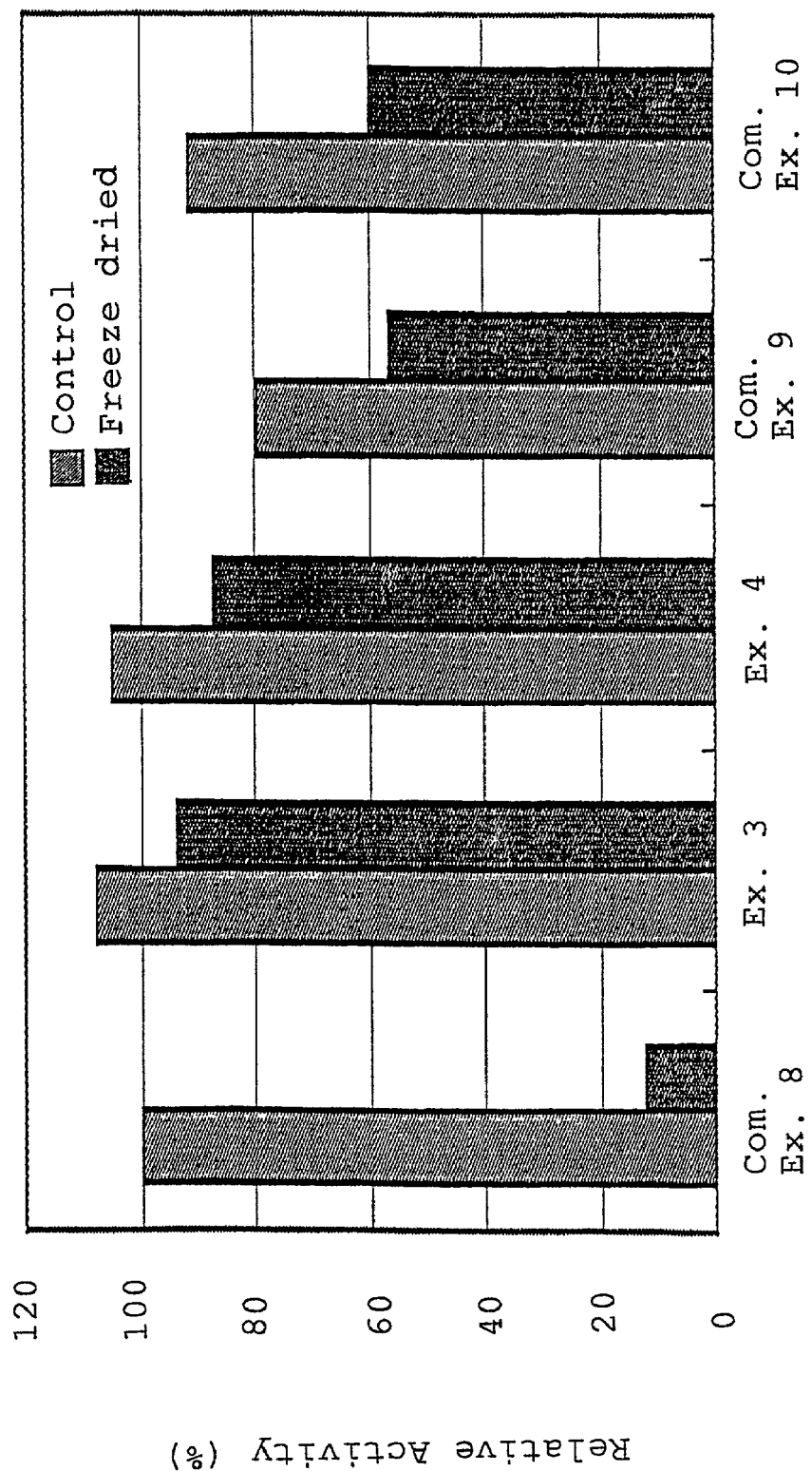
FIG. 2 shows the effect of inositol and trehalose on the storage stability of a freeze-dried cell extract (wheat embryo extract), wherein Control shows a cell extract preserved for the same period of time as the sample in liquid nitrogen without freeze-drying, and Freeze-dried shows a cell extract preserved at 37° C. for 24 h after freeze-drying.

As shown in FIG. 2, the freeze-dried compositions (Examples 3 and 4) containing myo-inositol retained activity of 80% or above even after preservation at 37° C. for 24 h. The freeze-dried compositions (Comparative Examples 9 and 10) containing trehalose showed an activity decrease to about 60%. Therefore, it is evident that myo-inositol is far superior to trehalose as a stabilizer of cell extract.

[Continuous Cell-Free Protein Synthesis by Dialysis Method Using Freeze-Dried Composition]

EXAMPLE 5 AND COMPARATIVE EXAMPLE 11

In the same manner as in Example 1, the respective freeze-dried compositions shown in Table 3 were prepared (sterile distilled water was used instead of the aqueous solution containing additives in Comparative Example 11).

TABLE 3

| | additive | mixture final concentration | | freeze-dried composition content | |
|---|---|---|---|---|---|
| | | additive wt % | protein wt % | additive wt % | protein wt % |
| Example 1 | myo-inositol | 5.50 | 2.75 | 64.8 | 32.4 |
| Comp. Ex. 11 | not added | — | 2.75 | — | 92.0 |

Figure 3:
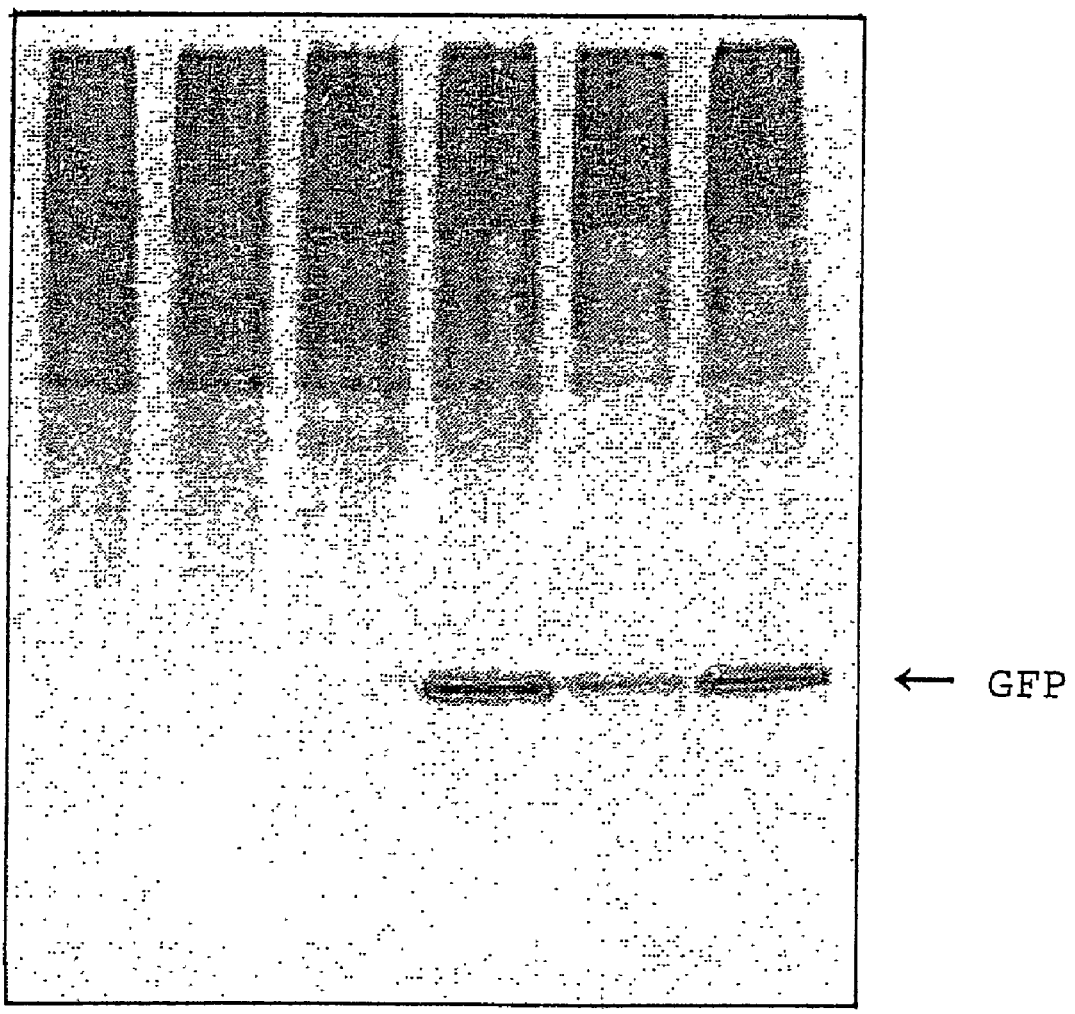
FIG. 3 is an electropherogram showing the result of continuous cell-free protein synthesis by a dialysis method using a freeze-dried cell extract (wheat embryo extract), wherein (before protein synthesis)
  lane 1: control, lane 2: Comparative Example 11,
  lane 3: Example 5
(after protein synthesis)
  lane 4: control, lane 5: Comparative Example 11,
  lane 6: Example 5
GFP: Green fluorescent protein.

Using the respective freeze-dried compositions shown in Table 3, cell-free protein synthesis was conducted in a continuous system. The cell-free protein synthesis in the continuous system followed the paper of Endo et al. (Y. Endo et al., J. Biotech., 25, 221–230 (1992) and K. Madin et al., PNAS, 97(2), 559–564 (2000)). The respective freeze-dried compositions shown in Table 3 were preserved at 37° C. for 24 h and, using these, reaction solution A in the above-mentioned batch activity assay method was prepared. The reaction solution A was placed in Dispo Dialyzer (Bio-Tech dialysis cup MWCO12000; Daiichi Pure Chemicals Co., Ltd.) and dialyzed against a dialysis external solution (20 mM HEPES-KOH (pH 7.6), 95 mM potassium acetate, 2.65 mM magnesium acetate, 4 mM dithiothreitol, 1.2 mM ATP, 0.25 mM GTP, 16 mM creatine phosphate, 0.38 mM spermidine, 20 kinds of L-amino acids (each 0.3 mM), 0.005% (w/v) sodium azide) in a 10-fold the volume of the reaction solution A. During dialysis, the solution was stirred with a stirrer at 26° C., and exchanged with a fresh external solution every 24 h. In addition, mRNA was supplied every 24 h to achieve 80 μg/ml. The protein synthesis was analyzed by separating 1 μl of the reaction mixture 48 h after synthesis, and after cataphoresis under non-denaturation conditions, stained with Coomassie brilliant blue and detected. The results are shown in FIG. 3. As a control, a wheat embryo extract in the same lot, which had been preserved in liquid nitrogen was used for continuous protein synthesis in the same manner.

As shown in FIG. 3, the freeze-dried composition (Example 5: lane 6) containing myo-inositol contained almost the same synthesized protein as the control (lane 4). The freeze-dried composition (Comparative Example 11: lane 5) without myo-inositol showed protein synthesis but apparently in a smaller synthesis amount as compared to control, suggesting a considerable decrease in the protein synthesis activity of the cell extract.

[Effect of Inositol on the Storage Stability of Creatine (Phospho)kinase Addition System]

EXAMPLES 6 AND 7

The sterile distilled water (16.5 μl, Example 6) or creatine (phospho)kinase (Cr—K) aqueous solution (16.5 μl, Example 7, 10 mg/ml) prepared by dissolving Cr—K (Roche) in sterile distilled water was added to 100 μl of the wheat embryo extract of Production Example 1, and respective freeze-dried compositions (Example 6 and 7) shown in Table 4 were prepared in the same manner as in Example 1.

TABLE 4

|  | additive | mixture final concentration | | | freeze-dried composition content | | |
| --- | --- | --- | --- | --- | --- | --- | --- |
|  |  | additive wt % | protein wt % | Cr—K wt % | additive wt % | protein wt % | Cr—K wt % |
| Example 6 | myo-inositol | 2.50 | 2.75 | — | 45.5 | 50.0 | — |
| Example 7 | myo-inositol | 2.50 | 2.75 | 0.08 | 44.9 | 49.3 | 1.5 |

(Storage Stability Test)

The respective freeze-dried compositions shown in Table 4 were preserved at 37° C. for 24 h and, according to the above-mentioned batch activity assay method, the cell-free protein synthesis activity of each freeze-dried composition was measured. The composition containing Cr—K (Example 7) was free of addition of Cr—K during assay. The results are shown in FIG. 4.

Figure 4:
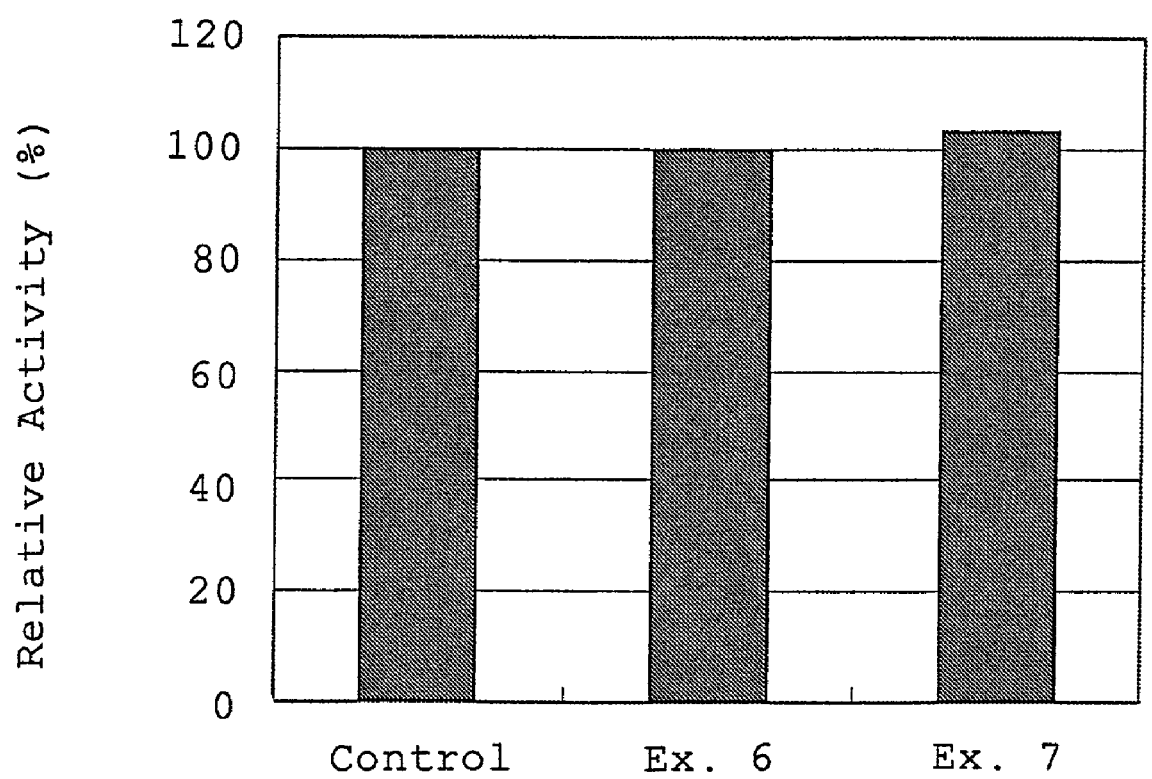
FIG. 4 shows the effect of inositol on the storage stability of a freeze-dried cell extract (wheat embryo extract) containing creatine (phospho)kinase, wherein Control shows a cell extract preserved for the same period of time as the sample in liquid nitrogen without freeze-drying.

As shown in FIG. 4, the composition containing Cr—K (Example 7) retained almost 100% activity. While the results are not shown, when cell-free protein synthesis was conducted without adding Cr—K to the reaction mixture, the protein synthesis activity was 1/10 or lower.

[Effect of Deliquescent Material on Freeze-Dried Composition]

EXAMPLES 8–10 AND COMPARATIVE EXAMPLE 12

In Production Example 1, a wheat embryo extract (potassium acetate (KOAc) (–) extract) was prepared using a final buffer without KOAc. In the same manner as in Example 1 except that KOAc(–) extract was used, respective freeze-dried compositions (Examples 8–10) shown in Table 5 were prepared (sterile distilled water was used instead of the aqueous solution containing additives in Example 8). Comparative Example 12 was prepared in the same manner as in Example 1 using a wheat embryo extract (KOAc(+) extract) prepared using a final buffer containing KOAc and sterile distilled water instead of an aqueous solution containing additives.

TABLE 5

|  | additive | mixture final concentration | | | freeze-dried composition content | | |
| --- | --- | --- | --- | --- | --- | --- | --- |
|  |  | additive wt % | protein wt % | KOAc mM | additive wt % | protein mM | KOAc |
| Example 8 | not added | — | 2.75 | 0.0 | — | 95.5 | 0.0 |
| Example 9 | myo-inositol | 2.75 | 2.75 | 0.0 | 48.8 | 48.8 | 0.0 |
| Example 10 | trehalose | 2.75 | 2.75 | 0.0 | 48.8 | 48.8 | 0.0 |
| Comp. Ex. 12 | not added | — | 2.75 | 0.1 | — | 92.0 | 3.7 |

(Storage Stability Test)

The respective freeze-dried compositions shown in Table 5 were preserved at 37° C. for 48 h and, according to the above-mentioned batch activity assay method, the cell-free protein synthesis activity of each freeze-dried composition was measured. The results are shown in FIG. 5.

Figure 5:
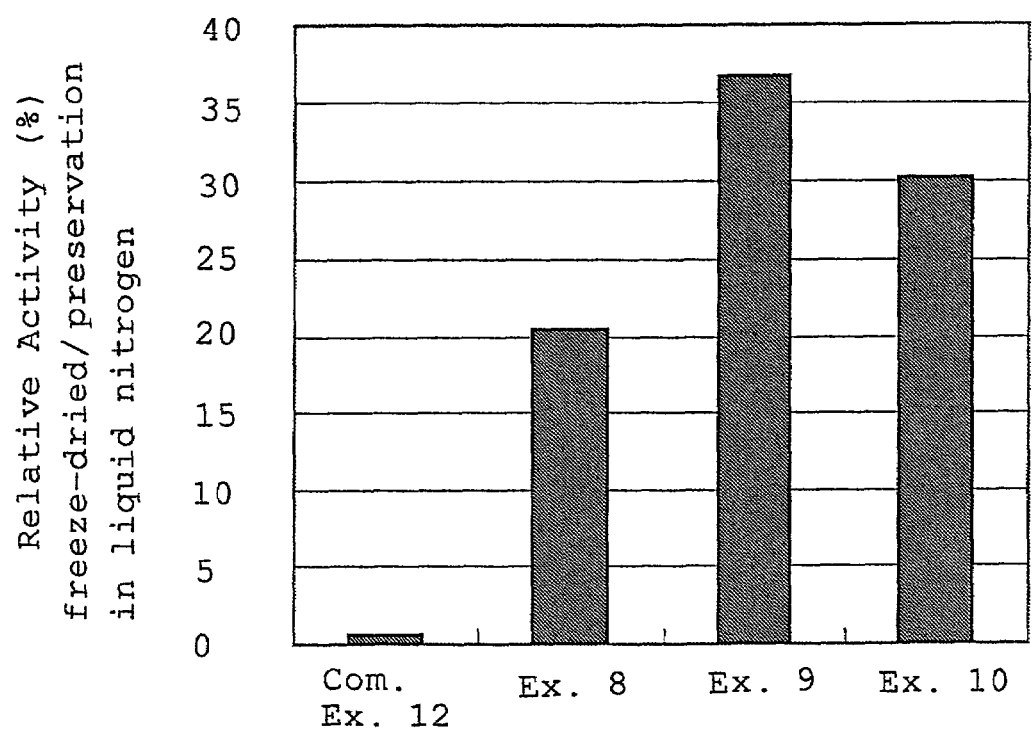
FIG. 5 shows the effect of a deliquescent material on the storage stability of a freeze-dried cell extract (wheat embryo extract).

As shown in FIG. 5, the freeze-dried composition (Comparative Example 12) containing KOAc nearly lost the activity, but the freeze-dried composition (Example 8) without KOAc showed about 20% of residual activity was found. In addition, the freeze-dried composition (Example 9) containing inositol but without KOAc retained the activity by 36%, which was the highest storage stability of the freeze-dried compositions subjected to the test.

[Synergistic Effect of Additives on Storage Stability of Freeze-Dried Composition]

EXAMPLES 11–14, COMPARATIVE EXAMPLES 13 AND 14

The respective freeze-dried compositions shown in Table 6 were prepared in the same manner as in Example 1 using the above-mentioned KOAc(–) extract (sterile distilled water was used instead of the aqueous solution containing additives in Comparative Example 13).

TABLE 6

|  | additive | mixture final concentration | | freeze-dried composition content | |
| --- | --- | --- | --- | --- | --- |
|  |  | additive wt % | protein wt % | additive wt % | protein wt % |
| Example 11 | myo-inositol | 2.75 | 2.75 | 49.0 | 49.0 |
| Example 12 | myo-inositol trehalose | each 2.75 | 2.75 | each 33.0 | each 33.0 |
| Example 13 | myo-inositol mannitol | each 2.75 | 2.75 | each 33.0 | each 33.0 |
| Example 14 | myo-inositol Ficoll 400 | each 2.75 | 2.75 | each 33.0 | each 33.0 |
| Comp. Ex. 13 | Not added | — | 2.75 | — | 95.0 |
| Comp. Ex. 14 | myo-inositol glucitol | each 2.75 | 2.75 | each 33.0 | each 33.0 |

(Storage Stability Test)

The respective freeze-dried compositions shown in Table 6 were preserved at 37° C. for 48 h and, according to the above-mentioned batch activity assay method, the cell-free protein synthesis activity of each freeze-dried composition was measured. The results are shown in FIG. 6.

Figure 6:
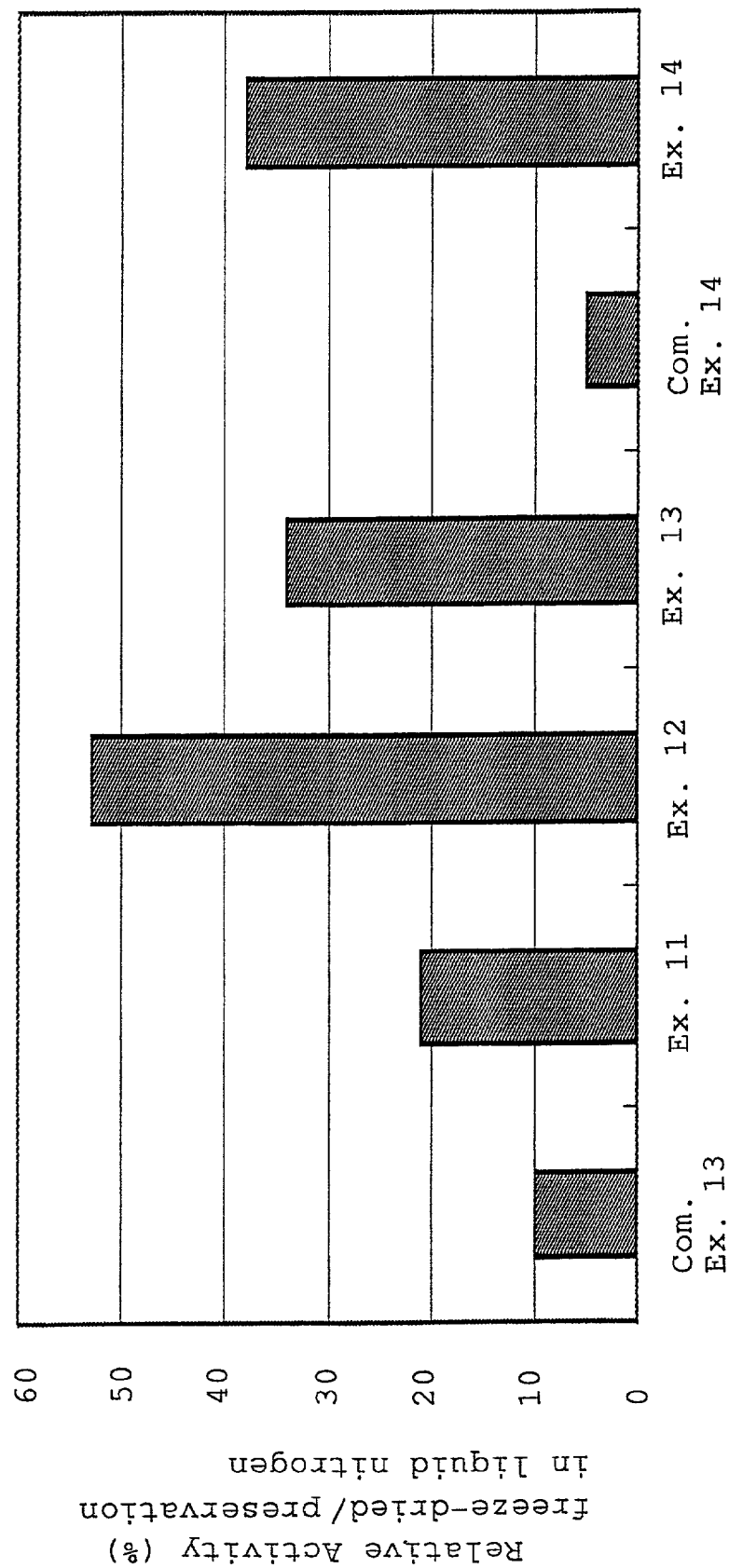
FIG. 6 shows a synergistic effect of an additive on the storage stability of a freeze-dried cell extract (wheat embryo extract).

As shown in FIG. 6, the freeze-dried composition (Comparative Example 11) containing myo-inositol alone showed 20% residual activity, but the freeze-dried composition (Example 12) further containing trehalose showed 52% residual activity and the freeze-dried composition (Example 13) containing mannitol showed 34% residual activity and the freeze-dried composition (Example 14) containing Ficoll 400 showed 38% residual activity, confirming the synergistic effect. In contrast, the freeze-dried composition (Comparative Example 14) containing myo-inositol and glucitol showed a negative effect.

[Effect of Each Polyhydric Alcohol on Storage Stability of Frozen Cell Extract (Wheat Embryo Extract)]

EXAMPLES 15–21 AND COMPARATIVE EXAMPLE 15

To wheat embryo extract (100 µl) prepared according to the method of Production Example 1 was added each additive to the final concentration of each additive as shown in Table 7, and the mixture was frozen at −15° C. to give each frozen wheat embryo extract composition (hereinafter to be referred to as a frozen composition).

TABLE 7

| | | mixture final concentration | |
|---|---|---|---|
| | additive | additive wt % | protein wt % |
| Example 15 | myo-inositol | 2.75 | 2.75 |
| Example 16 | trehalose | 2.75 | 2.75 |
| Example 17 | mannitol | 2.75 | 2.75 |
| Example 18 | glucitol | 2.75 | 2.75 |
| Example 19 | xylitol | 2.75 | 2.75 |
| Example 20 | sucrose | 2.75 | 2.75 |
| Example 21 | Ficoll 400 | 2.75 | 2.75 |
| Comp. Ex. 15 | not added | — | 2.75 |

(Storage Stability Test)

The respective frozen compositions were left standing at −15° C. for 1 week. According to the above-mentioned batch activity assay method, the cell-free protein synthesis activity of each frozen composition was measured. The results are shown in FIG. 7.

Figure 7:
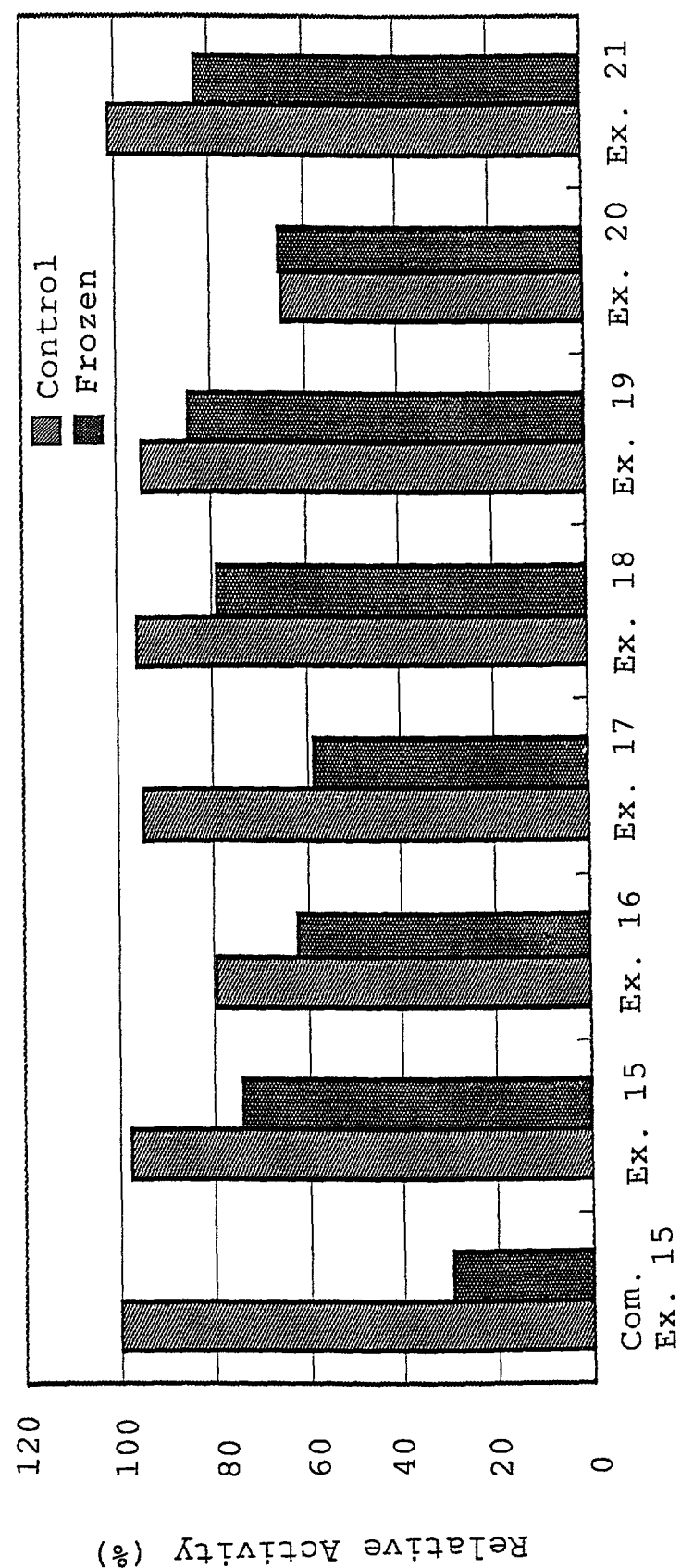
FIG. 7 shows the effect of each additive on the storage stability of a freeze-dried cell extract (wheat embryo extract), wherein Control shows a cell extract preserved for the same period of time as the sample in liquid nitrogen without freezing, and Frozen shows a cell extract preserved at −15° C. for one week.

As shown in FIG. 7, the frozen composition without polyhydric alcohol (Comparative Example 15) showed the activity decreased to about 30% but the frozen compositions containing polyhydric alcohol (Examples 15–21) retained the activity by 55% or above. Particularly, the frozen compositions containing inositol (Example 15), glucitol (Example 18), xylitol (Example 19) and Ficoll 400 (Example 21) retained the activity by 70% or above.

The freeze-dryable or freeze-dried composition for cell-free protein synthesis of the present invention containing inositol as a stabilizer, or a deliquescent material in a proportion of not more than 0.01 part by weight per part by weight of protein in the composition, shows superior storage stability in a freeze-dried state. The freezable or frozen composition for cell-free protein synthesis of the present invention containing polyhydric alcohol as a stabilizer shows superior storage stability in a frozen state. According to the present invention, therefore, a composition for cell-free protein synthesis can be supplied more easily and more conveniently than ever.

What is claimed is:

1. A freeze-dried composition for cell-free protein synthesis, which comprises a wheat germ extract containing components for cell-free protein synthesis including ribosomes and tRNA, and an inositol.

2. The composition of claim 1, wherein the inositol is contained in a proportion of 0.3–3 parts by weight per part by weight of a protein in the composition.

3. The composition of claim 1, which further comprises at least one component selected from the group consisting of trehalose, mannitol and sucrose-epichlorohydrin copolymer.

4. The composition of claim 1, which further comprises a deliquescent material, wherein the deliquescent material is contained in a proportion of not more than 0.01 part by weight per part by weight of a protein in the composition.

5. The composition of claim 4, wherein the deliquescent material is potassium acetate and/or magnesium acetate.

6. The composition of claim 1, which further comprises a bioactive protein involved in cell-free protein synthesis.

7. The composition of claim 6, wherein the bioactive protein is at least one protein selected from the group consisting of creatine (phospho)kinase, pyruvate kinase, RNA polymerase and chaperone protein.

8. A method of cell-free protein synthesis, comprising adding the composition of claim 1 to a reaction system containing mRNA encoding an objective protein, amino acids and an energy source to create a reaction mixture and heating the reaction mixture whereby the objective protein is synthesized.

9. The method of claim 8, which is conducted in a continuous supply system of amino acids and energy sources.

10. The method of claim 9, wherein the continuous supply system of amino acids and energy sources is based on a dialysis method.

* * * * *